US009896683B2

(12) United States Patent
Ambros et al.

(10) Patent No.: US 9,896,683 B2
(45) Date of Patent: Feb. 20, 2018

(54) ISOLATING CIRCULATING MICRORNA (MIRNA)

(71) Applicants: University of Massachusetts, Boston, MA (US); Firefly Bioworks, Cambridge, MA (US)

(72) Inventors: Victor Ambros, Hanover, NH (US); Rosalind Lee, Hanover, NH (US); Anthony Patrick Fusco, Westwood, MA (US)

(73) Assignees: University of Massachusetts, Boston, MA (US); Firefly BioWorks, Cambridge, MA (US)

( * ) Notice: Subject to any disclaimer, the term of this patent is extended or adjusted under 35 U.S.C. 154(b) by 249 days.

(21) Appl. No.: 14/812,694

(22) Filed: Jul. 29, 2015

(65) Prior Publication Data

US 2016/0032277 A1 Feb. 4, 2016

Related U.S. Application Data

(60) Provisional application No. 62/030,773, filed on Jul. 30, 2014.

(51) Int. Cl.
*C12P 19/34* (2006.01)
*C12N 15/10* (2006.01)
*C12Q 1/68* (2018.01)

(52) U.S. Cl.
CPC ..... *C12N 15/1013* (2013.01); *C12N 15/1006* (2013.01); *C12N 15/1017* (2013.01); *C12Q 1/6806* (2013.01); *C12Q 1/6883* (2013.01); *C12Q 2600/158* (2013.01); *C12Q 2600/178* (2013.01)

(58) Field of Classification Search
CPC ............ C12Q 1/6806; C12Q 2527/125; C12Q 1/6883; C12Q 2600/158; C12Q 2600/178; C12N 15/1017; C12N 15/1013; C12N 15/1006
USPC ...................................................... 435/91.2
See application file for complete search history.

(56) References Cited

U.S. PATENT DOCUMENTS

2015/0045237 A1* 2/2015 Landthaler ........... C12Q 1/6804 506/4

OTHER PUBLICATIONS

Moldovan et al., J. Cell. Mol. Med., vol. 18, No. 3, pp. 371-390, 2014.*
Parikh et al., Methods Mol. Biol. vol. 1024, pp. 157-172, 2013.*
Tan et al., Journal of Biomedicine and Biotechnology, vol. 2009, article ID 574398, pp. 1-10, 2009.*
Ambros, "microRNAs: Tiny Regulators with Great Potential", Cell, vol. 107:823-826 (2001).
Fichtlscherer et al., "Circulating MicroRNAs in Patiennts With Coronary Artery Disease", Circulation Research, vol. 107:677-684 (2010).
Ganepola et al., "Novel blood-based microRNA biomarker panel for early diagnosis of pancreatic cancer", World Journal of Gastrointestinal Oncology, vol. 6:22-33 (2014).
Ji et al., "miR-574-5p negatively regulates *Qki6/7* to impact β-*catenin/Wnt* signaling and the development of colorectal cancer", Gut, vol. 62:716-726 (2013).
Kosaka et al., "Circulating microRNA in body fluid: a new potential biomarker for cancer diagnosis and prognosis", Cancer Science, vol. 101:2087-2092 (2010).
Kozomara et al., "miRBase: annotating high confidence microRNAs using deep sequencing data", Nucleic Acids Res., vol. 42:D68-73 (2014).
Landgraf et al., "A Mammalian microRNA Expression Atlas Based on Small RNA Library Sequencing", Cell, vol. 129:1401-1414 (2007).
Laterza et al., "Plasma MicroRNAs as Sensitive and Specific Biomarkers of Tissue Injury", Clinical Chemistry, vol. 55:1977-1983 (2009).
Leidinger et al., "A blood based 12-miRNA signature of Alzheimer disease patients", Genome Biology, vol. 14:478 (2013).
Liu et al., "Serum MicroRNA Expression Profile as a Biomarker in the Diagnosis and Prognosis of Pancreatic Cancer", Clinical Chemistry, vol. 58:610-618 (2012).
Madhavan et al., "Cancer diagnosis and prognosis decoded by blood-based circulating microRNA signatures", frontiers in Genetics, vol. 4, Article 116 (2013).
Pritchard et al., "Blood Cell Origin of Circulating MicroRNAs: A Cautionary Note for Cancer Biomarker Studies", Cancer Prev Res, vol. 5:492-497 (2012).
Schee et al., "Deep Sequencing the MicroRNA Transcriptome in Colorectal Cancer", PLoS One, vol. 8:e66165 (2013).
Siegel et al., "Circulating microRNAs involved in multiple sclerosis", vol. 39:6219-6225 (2012).
Siow et al., "Spotlight issue: MicroRNAs in the microcirculation—from cellular mechanisms to clinical markers", Microcirculation, vol. 19:193-195 (2012).
Starkey Lewis et al., "Circulating MicroRNAs as Potential Markers of Human Drug-Induced Liver Injury", Hepatology, vol. 54:1767-1776 (2011).
Valadi et al., "Exosome-mediated transfer of mRNAs and microRNAs is a novel mechanism of genetic exchange between cells", Nature Cell Biology, vol. 9:654-659 (2007).
Vickers et al., "MicroRNAs are transported in plasma and delivered to recipient cells by high-density lipoproteins", Nature Cell Biology, vol. 13:423-433 (2011).
Wang et al., "Circulating microRNAs, potential biomarkers for drug induced liver injury", Proc Natl Acad Sci USA, vol. 106:4402-4407 (2009).
Wang et al., "Comparing the MicroRNA Spectrum between Serum and Plasma", PLoS One, vol. 7:e41561 (2012).
Ward et al., "Circulating Cell and Plasma microRNA Profiles Differ between Non-ST-Segment and ST-Segment-Elevation Myocardial Infarction", Fam Med Med Sci Res., vol. 2:108 (2013).

(Continued)

*Primary Examiner* — Cynthia B Wilder
(74) *Attorney, Agent, or Firm* — Fish & Richardson P.C.

(57) ABSTRACT

Methods for isolating circulating small RNAs, e.g., microRNA (miRNA), from plasma samples, e.g., that comprise using an alkaline phenol:chloroform extraction, and methods of use thereof, including for the detection, prognosis, and/or monitoring of disease in a subject.

18 Claims, 6 Drawing Sheets

(56) References Cited

OTHER PUBLICATIONS

Ward et al., "Plasma microRNA profiles distinguish lethal injury in acetaminophen toxicity: A research study", World J Gastroenterol, vol. 18:2798-2804 (2012).
Willeit et al., "265 Plasma MicroRNAs as Biomarkers for Platelet Inhibition", Heart, vol. 99:A139-A140 (2013).
Zampetaki et al., "Plasma MicroRNA Profiling Reveals Loss of Endothelial MiR-126 and Other MicroRNAs in Type 2 Diabetes", Circulation Research, vol. 107:810-817 (2010).

* cited by examiner

ISOLATING CIRCULATING MICRORNA (MIRNA)

CLAIM OF PRIORITY

This application claims the benefit of U.S. Provisional Patent Application Ser. No. 62/030,773, filed on Jul. 30, 2014. The entire contents of the foregoing are hereby incorporated by reference.

FEDERALLY SPONSORED RESEARCH

This invention was made with U.S. Government support under Grant No. GM034028 awarded by the National Institutes of Health. The Government has certain rights in the invention.

TECHNICAL FIELD

The present invention relates to methods for isolating circulating small RNAs, e.g., microRNA (miRNA), from plasma samples, and methods of use thereof, including for the detection, prognosis, and/or monitoring of disease in a subject.

BACKGROUND

MicroRNAs are small regulatory RNAs present in all animal cells. Many microRNAs have been shown to be involved in human disease. Information about the disease status of a patient can be obtained by quantitative analysis of the levels of specific microRNAs in normal and diseased tissue, or in body fluids such as blood serum/plasma, cerebrospinal fluid, or urine. Detection of circulating miRNAs in blood plasma or other biological fluids promises to provide a convenient, inexpensive, and noninvasive way to diagnose and/or track the progress of treatment of diseases that are currently difficult to diagnose or successfully treat.

SUMMARY

At least in part, the present invention is based on the development of novel methods for extraction of small RNAs from biological fluid samples, e.g., plasma samples; these methods significantly increase the yield of many assayable small RNAs such as miRNA, some by tenfold or more over present standard methods.

Thus, in a first aspect, the invention provides methods for isolating RNA from a sample, e.g., a sample of a biological fluid, e.g., blood, plasma or serum, urine, CSF or other fluid, e.g., from a human subject. The methods include digesting the sample with Proteinase K in the presence of chaotropic salts and detergent; extracting RNA from the sample using an alkaline phenol:chloroform, e.g., at pH 7-9, preferably pH 8.0, extraction step; and isolating the extracted RNA from the sample.

In some embodiments, extracting RNA from the sample using alkaline phenol:chloroform extraction step comprises contacting the sample with a solution comprising nuclease free water and phenol:chloroform, at a ratio of at least 1:10, 1:5, 1:2, or 1:1 (vol:vol) of nuclease free water to phenol:chloroform; in some embodiments, at least an equal volume of nuclease free water and phenol:chloroform is used. The extraction step can also include mixing the sample, e.g., by shaking or agitation, and allowing the aqueous and organic phases to separate, optionally by centrifuging the sample. Additional water can optionally be added, e.g., to make a ratio of about 1.5:1 or 2:1 water to phenol:choloform.

In some embodiments, the phenol:chloroform ratio is between 6:1 to 1:1, e.g., 5:1 to 3:1, preferably 5:1.

In some embodiments, lysing the sample comprises contacting the sample with a detergent buffer in the presence of Proteinase K, e.g., at least 4, 5, 6, or 7 mAU of Proteinase K, preferably at least 6 mAU of Proteinase K.

In some embodiments, the detergent buffer is a guanidine buffer.

In some embodiments, the guanidine buffer comprises Guanidine HCl 2M; Triton 1.6% (vol/vol); Tween 20 1.6% (vol/vol); EDTA 37.5 mM; and Tris pH 8.0 37.5 mM.

In some embodiments, isolating the extracted RNA from the sample comprises one or more of ethanol extraction; magnetic bead separation; or spin column extraction.

In another aspect, the invention provides methods for detecting a level of a circulating miRNA in a subject. The methods include providing a sample comprising plasma or serum from a subject, e.g., from a human subject;
lysing the sample;
extracting RNA from the sample using an alkaline phenol:chloroform extraction step, e.g., using pH 7-9, preferably pH 8.0 phenol:chloroform;
isolating the extracted RNA from the sample;
and determining a level of the miRNA in the extracted RNA.

In some embodiments, determining a level of the miRNA in the extracted RNA comprises amplifying the miRNA, e.g. using PCR, e.g., using qRT-PCR; sequencing the RNA; hybridization; or a gene chip.

In some embodiments of the methods described herein, chloroform substitutes can be used in place of chloroform, e.g., 1-Bromo-3-chloropropane.

In yet a further aspect, the invention features methods for monitoring a level of a miRNA in a subject, e.g., a mammalian subject, e.g., a human subject. The methods include providing a first sample comprising plasma or serum of the human subject at a first time point; detecting a level of one or more circulating miRNAs in the first sample using a method described herein; providing a second sample comprising plasma or serum of the human subject at a second time point; detecting a level of the one or more circulating miRNAs in the second sample using the same method; and comparing the level of the miRNA in the first sample to the level of the miRNA in the second sample.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1A:
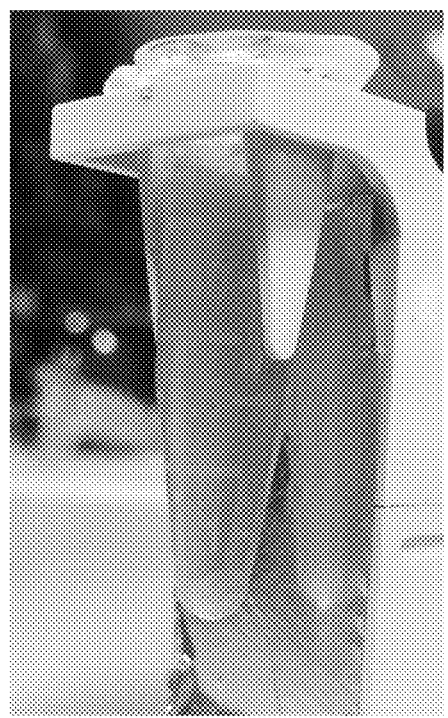
FIGS. 1A-D. Images of tubes containing samples in various stages of preparation using a method as described in Example 8. 1A, Pelleted debris from plasma. 1B, Normal interface. 1C, Too thick interface. 1D, Thick interface releases aqueous after re-spinning in a fresh tube.
Figure 1B:
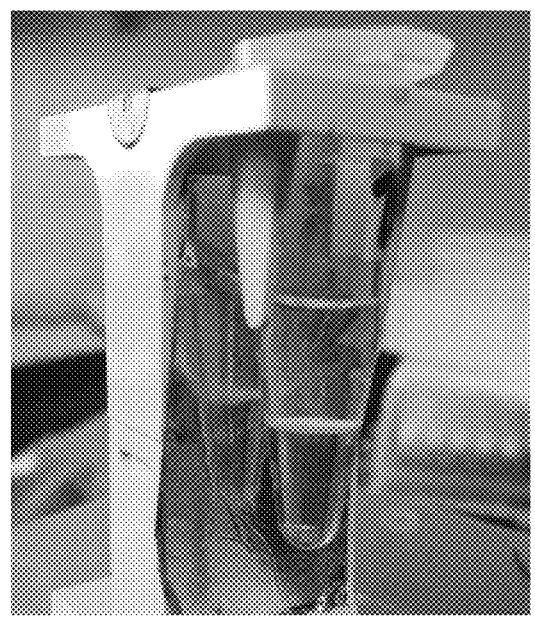
Figure 1C:
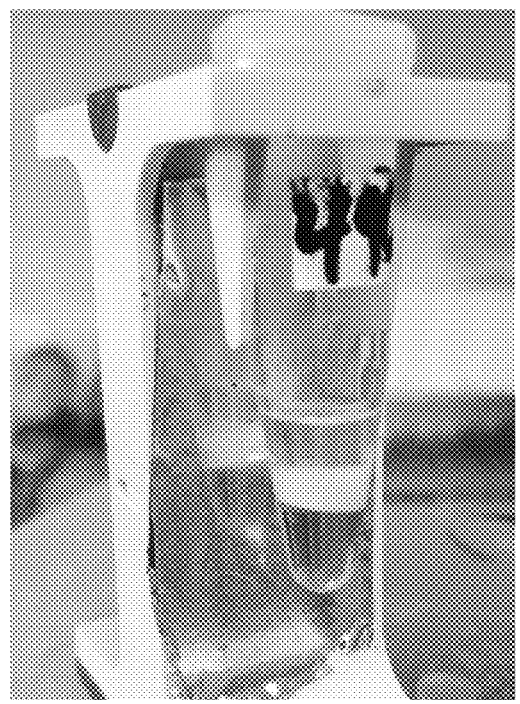
Figure 1D:
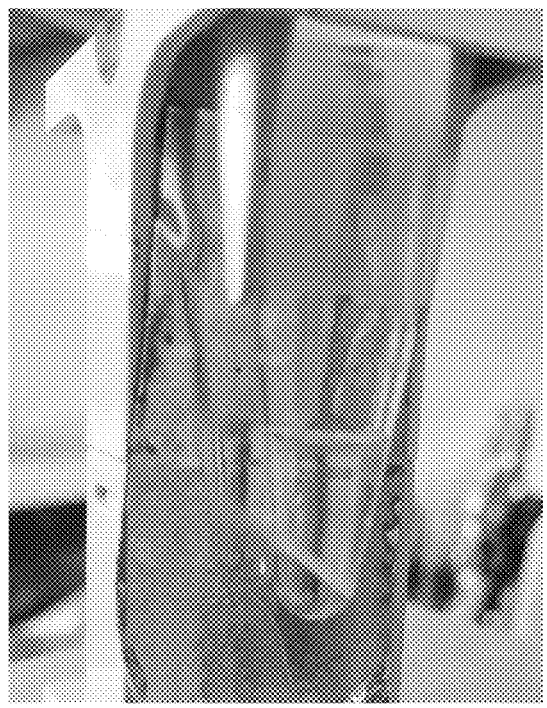

MicroRNAs (miRNAs) are short (~22 nt in length) regulatory RNAs that control gene expression post-transcriptionally (7, 8). The human genome contains more than 1000 genes encoding distinct miRNAs whose levels in a biological sample can be quantified with great sensitivity and precision using quantitative Real-Time PCR (qRT-PCR) (9). Many miRNAs are expressed tissue-specifically or enriched in certain cell types, with the expression pattern providing signatures for the physiological or pathological status of specific cells and tissues (10, 11). Importantly, miRNAs can be exported from cells and are detectable in stable complexes extracellularly, in blood, serum or plasma (12).

There is ample evidence that circulating extracellular miRNAs in blood can serve as biomarkers for internal organ physiology and pathology (11, 13, 14).

Isolation of Small RNAs from Biological Samples

Small RNAs (less than 200 nts) such as miRNAs are present in plasma at extremely small levels, in the picomolar range. However, they appear to be very stable and can be reproducibly isolated from samples that have undergone several freeze thaw cycles. The miRNAs are often found in different complexes, requiring a combination of approaches for isolation. Exogenous, spiked in miRNA is easily isolated because it is not complexed with proteins, while endogenous miRNAs require protease digestion followed by organic extraction. Biological samples such as plasma samples can vary greatly between patients so consistent small RNA isolation is challenging.

Previous methods typically use a simple Tri Reagent (organic) extraction followed by precipitation of nucleic acid onto filters, and then elution of the RNA with water. The present inventors have found that these previous methods are inefficient at recovering endogenous circulating small RNAs such as miRNAs from human plasma and serum, resulting in 10%, or poorer, yields. Moreover, distinct endogenous miRNAs were differentially resistant to Tri Reagent extraction, and their relative yields were affected by the physiological state of the subject (e.g., hydration, fasting, exercising, lipid content/high cholesterol). These shortcomings are overcome by the methods described herein for the isolation of RNA from biological samples, e.g., blood serum/plasma, cerebrospinal fluid, or urine.

An exemplary flow chart is shown in FIG. 6. The present methods can include one or more of the following features:

Use of a lysis buffer comprising a detergent (e.g., triton and/or tween) and chaotropic salts (e.g., guanidine HCl buffer) with Proteinase K digestion for lysis to completely release miRNAs prior to extraction, e.g., prior to organic extraction, e.g., without using Tri Reagent. An exemplary lysis buffer is described herein. Isolation without Proteinase K digestion results in a different profile so some miRNAs are in a robust protein complex that is not disrupted by organic extraction. Preferably, the lysis buffer includes one or both of a chelating agent (e.g., Ethylenediaminetetraacetic acid (EDTA)) and a buffer, e.g., tris(hydroxymethyl)aminomethane) (Tris) at a pH of about 8, e.g., 7.5-9. In some embodiments, the buffer does not contain metal salts such as lithium acetate, transition metals, reducing agents (e.g., thiol-containing reducing agents), or b-mercaptoethanol.

Use of an alkaline phenol:chloroform extraction step, e.g., using pH 7-9, preferably pH 8.0 phenol:choloform (i.e., phenol:choloform in a ratio between 6:1 to 1:1, e.g., 5:1 to 3:1, preferably 5:1 volume:volume). RNA is acid stable so buffers routinely are brought to pH 4.5. As shown herein, using alkaline phenol:choloform (e.g., pH 7-9, preferably pH8) doubles the yield.

Additional water in phenol extraction step. Because human blood samples vary greatly according to lipid and protein content, it was difficult to get a reliable yield of purified RNA. The additional water (e.g., at least 1:1 ratio of water volume to volume of phenol:chloroform, or 1.5:1 or 2:1 water to phenol:chloroform) in the phenol extraction step allows more consistent separation of the organic and aqueous phases. It also dilutes the lysis buffer concentration (desirable for optimal digestion) and prevents co precipitation of contaminants from the buffer. The concentration of the buffer components was determined empirically.

In addition, the methods can use one of the following concentration/purification methods:

Use of small volume silica purification columns, e.g., tini columns from Enzymax, instead of the standard purification columns. The amount of RNA in plasma/serum is so small that it remains on the standard silica filter (used by all commercial purification kits) during the elution process, causing great loss in yield.

Use of magnetic beads, e.g., silicon-coated magnetic beads, to recover ethanol-precipitated nucleic acids immediately following the organic extraction steps. Magnetic beads allow for more complete washing and increased efficiency of RNA elution compared to glass filters.

The present methods can be used on any sample, e.g., a sample from a biological fluid such as blood, serum, plasma, urine, saliva, CSF, tears, semen, vaginal fluid, and so on. This method can also be used on tissue from an organism; an in vitro culture; or other sample, if standard sized silica columns are used to accommodate the greater yield.

Diagnosis and Monitoring

The methods described herein can be used to obtain miRNA for clinical and research purposes; for example, the methods can be used to isolate miRNAs for diagnosis and monitoring of disease. For example, the present methods can be used to isolate miRNA from a sample to detect the presence of cancer or to aid in prognosis or monitoring of treatment efficacy; see, e.g., Tables 1-6 of Madhavan et al., Front Genet. 2013; 4:116 (incorporated by reference herein), which sets forth a number of miRNAs and their association with prostate (Table 1), breast (Table 2, e.g.,), lung (Table 3); Colorectal (Table 4); Gastric (Table 5) or hematological (Table 6) cancer; and Ganepola et al., World J Gastrointest Oncol 2014 Jan. 15; 6(1): 22-33 (which describes the association of miR-642b, miR-885-5p, and miR-22 with cancer); see also Table 1 and FIG. 1 of Kosaka et al., Cancer Sci 2010; 101: 2087-2092 (incorporated by reference herein). Leidinger et al., Genome Biology 2013, 14:R78 (incorporated by reference herein), described a blood based 12-miRNA signature associated with Alzheimer's disease. See also Ji S et al. (2013) miR-574-5p negatively regulates Qki6/7 to impact β-catenin/Wnt signalling and the development of colorectal cancer. Gut 62:716-726; Liu R et al. (2012) Serum microRNA expression profile as a biomarker in the diagnosis and prognosis of pancreatic cancer. Clin Chem 58:610-618; Ward J A et al. (2013) Circulating Cell and Plasma microRNA Profiles Differ between Non-ST-Segment and ST-Segment-Elevation Myocardial Infarction. Fam Med Med Sci Res 2:108; Ward J, Bala S, Petrasek J, Szabo G (2012) Plasma microRNA profiles distinguish lethal injury in acetaminophen toxicity: a research study. World J Gastroenterol 18:2798-2804; Laterza O F et al. (2009) Plasma MicroRNAs as sensitive and specific biomarkers of tissue injury. Clin Chem 55:1977-1983; Wang K et al. (2009) Circulating microRNAs, potential biomarkers for drug-induced liver injury. Proc Natl Acad Sci USA 106:4402-4407; Starkey Lewis P J et al. (2011) Circulating microRNAs as potential markers of human drug-induced liver injury. Hepatology 54:1767-1776; 265 Plasma Micrornas As Biomarkers For Platelet Inhibition (2013) 265 PLASMA MICRORNAS AS BIOMARKERS FOR PLATELET INHIBITION. Heart 99:A139-A140; and Pritchard C C et al. (2012) Blood cell origin of circulating microRNAs: a cautionary note for cancer biomarker studies. Cancer Prey Res (Phila) 5:492-497. In addition, the methods can be used to obtain miRNAs for diagnosis of coronary artery disease (see, e.g., Fichtlscherer et al., Circulation Research. 2010; 107:677-684); type 2 diabetes (e.g., miR-126, see, e.g., Zampetaki et al., Circulation Research. 2010; 107:810-817); multiple sclerosis (see, e.g., Siegel et al., Molecular Biology Reports 2012; 39(5):6219-6225)

Kits

Also described herein are kits for use in a method described herein that include some or all of the reagents necessary to perform an isolation method described herein. For example, the kits can include some or all of the following, preferably in suitable containers:

Lysis buffer, e.g., 1× or concentrated (e.g., 2× or 3×);

PE buffer (2 mMTris pH 7.5, 20 mM NaCl, 80% ethanol (vol/vol))

Proteinase K, preferably >600 mAU/ml;

Spike-in small RNA, e.g., miRNA, e.g., arabadopsis mir-159a or cel-mir-39

Alkaline Phenol:chloroform in a ratio from 6:1 to 1:1, e.g., 5:1 to 3:1, preferably 5:1; at an alkaline pH, e.g., 7-9, e.g., pH 8.0.

In some embodiments, the kits also include nuclease-free water; nuclease free and optionally siliconized or low-bind tubes; a small-volume column (e.g., with an elution volume of <10 ul); polyacryl carrier; and/or magnetic beads, e.g., silica-coated magnetic beads.

EXAMPLES

The invention is further described in the following examples, which do not limit the scope of the invention described in the claims.

Materials & Methods

The following materials and methods were used in the example set forth below.

Lysis Buffer

| Ingredient | For 50 ml of lysis buffer | Approx. final concentration in plasma lysis |
|---|---|---|
| 6.4M Guanidine HCl | 30.6 g | 2M |
| 5% Triton (vol/vol) | 5 ml of 50% (vol/vol) solution in H2O | 1.6% (vol/vol) |
| 5% Tween 20 (vol/vol) | 5 ml of 50% (vol/vol) solution in H2O | 1.6% (vol/vol) |
| 120 mM EDTA | 12 ml of 0.5M Na2EDTA pH 8.0 | 37.5 mM |
| 120 mM Tris pH 8.0 | 3 ml of 2M Tris base pH 8.0 | 37.5 mM |

PE Buffer
2 mM Tris pH 7.5, 20 mM NaCl, 80% ethanol(vol/vol)

Example 1. Purification of Total RNA from Plasma or Serum

This example provides an exemplary method for purification of total RNA from plasma or serum, e.g., from human plasma or serum.

Step 1.

For Plasma, collect blood in EDTA-containing tubes (not heparin; any type of heparin tube contaminates the RNA irreversibly with reverse transcriptase inhibitor; blood from heparinized surgical patients cannot be used) with a large gauge needle (18-20 ga). Invert gently, without shaking, to reduce hemolysis. Store on ice until spun as soon as practical (ideally less than one hour) at 2000 g for 15 minutes to separate the plasma from the cells and buffy coat. Aliquot the plasma layer into standard microfuge tubes; store at −80° C. if necessary.

For Serum, collect blood with a large gauge needle in plain red top tubes and store on ice until the clot forms ~20 minutes. Spin at 2000 g for 15 minutes to compress the clot.

Step 2.

If frozen, thaw on ice. Pipet the serum/plasma into 1.7 ml micro centrifuge tubes and spin at >16,000 rpm (or highest speed) at 4° C. for 10 minutes to remove platelets and debris; a pellet of debris will form on the bottom and a layer of lipid can form on top. See FIG. 7A. Avoiding these two layers, aliquot the cleared serum/plasma into fresh tubes, preferably about 200 ul per aliquot. Store at −80° C. only if necessary.

Step 3.

Take 200 ul of the cleared serum/plasma (fresh or thawed on ice) and add to a 1.7 ml micro centrifuge tube containing 100 ul of lysis buffer, ~6 mAu Proteinase K (e.g., 10 ul of Proteinase K, >600 mAU/ml, such as Qiagen 19131), and (optional, don't use if sequencing) a spiked-in synthetic miRNA for quantification (e.g., arabadopsis mir-159a).

Vortex and incubate with maximum shaking at 65° C. for 15 minutes using a thermomixer such as the Eppendorf 5350

Step 4.

Cool to room temperature (about 20 to 23.5° C.), then add 250 ul of nuclease free water and 250 ul of phenol:chloroform 5:1, pH8.0. The alkaline pH (e.g., 7-9, e.g., 8.0) is critical in getting a good yield; using pH 4.5 decreases yield by up to 50%. The dilution of the organic lysis with water results in a cleaner interface and a higher yield.

Cap securely, and shake for 5 min at room temperature.

Step 5.

Centrifuge (preferably at room temperature) for 5 minutes at maximum speed (>16K rcf) in a micro centrifuge. A spinning bucket rotor centrifuge is preferred to aid in creating a compact interface. Spinning at refrigerated temperature creates large interfaces that make it difficult to cleanly recover the aqueous phase containing the RNA, so spinning at room temperature is preferred. See FIG. 7B.

If the interface is thick (>2 mm thick, see FIG. 7C), take the aqueous layer and the interface (leaving the phenol layer) and re-spin in a fresh 1.7 ml tube. This will collapse the interface and release more of the aqueous layer. Alternatively, add more water 50 ul at a time, shake and re-spin until the aqueous layer is approximately 450-500 ul. Remove the interface and aqueous to a clean tube and spin again See FIG. 1D.

Remove ~450-500 ul clean aqueous phase into a fresh 2 ml tube.

To concentrate or purify the RNA, one of the following options was used.

Option 1

Remove the aqueous layer (approximately 450-500 ul) to a clean 2 ml sized tube containing 7 ul of silica coated magnetic beads such as Qiagen MagAttract Suspension B. Invitrogen dynabeads can also be used, but they do not form as tight a pellet and are easily dislodged in the washing steps Vortex to resuspend, then add 1.5 ml of 4° C. 200 proof ethanol.

Shake at RT for 5 min. Do not put into the cold because contaminants will bind to the beads. Beads may clump.

Magnetize the beads and aspirate the liquid.

Wash twice with 500 ul 4° C. PE buffer: 2 mMTris pH 7.5, 20 mM NaCl, 80% ethanol(vol/vol), vortexing, magnetizing, and aspirating in between washes.

Let air dry briefly until the excess liquid around the beads evaporates.

Elute using 100 ul of RNAse free water with shaking at 70° C. for 60 seconds.

Magnetize and remove liquid to a clean, 1.7 ml low bind or siliconized microcentrifuge tube containing 2 ul of polyacryl carrier (MRCgene.com cat# PC 152) and 22 ul of 3M NaAc pH 5.0.

Repeat the extraction with another 100 ul of water and add to the previous tube.

Vortex then add 3 volumes (660 ul) of 100% ethanol

Place in −80° C. freezer until solid (20 minutes), or overnight.

Spin at highest speed for 20 minutes at 4° C. Carefully remove liquid. Pellet will be very small and loose. RNA may also be streaking up the side of the tube. Add 200 ul of 4° C. 80% ethanol:water (vol/vol) and vortex. Respin for 10 minutes.

Remove the liquid and air dry until just damp (not totally dry). Pellet can be very loose from fragments coming off the sides.

Resuspend in 10 ul of RNAse free water and store at −80° C.

Option 2

Add 3× volume (e.g., 1.5 ml) of 4° C. 200 proof ethanol to the aqueous layer and vortex briefly to mix. Do not put on ice, as insoluble contaminants can form at low temperatures.

Pipet the liquid into a mini silica based purification column that has an elution volume of less than 10 ul, e.g., columns from Enzymax (Tini Spin) or Zymo Research (Zymo-Spin1). The larger membranes on standard sized purification columns retain contaminants after the washes and do not release the RNA, greatly reducing the yield and quality of the fmolar amounts of RNA.

Spin the fluid through the column at low speed (~3K rcf) for 30 seconds. Discard the flow through. Reload and spin the column until all of the sample has been loaded.

Wash twice with 500 ul 4° C. PE buffer: 2 mMTris pH 7.5, 20 mM NaCl, 80% (vol/vol) ethanol.

Put in a wash tube and spin in a microfuge for 2 minutes at top speed to dry.

Place in a new tube and add 6 ul of heated (65 degree C.) RNAse free water. Let sit for a minute, and then spin at top speed for one minute. Repeat elution with another 6 ul of RNAse free water into the same tube. Store RNA at −80° C.

Alternatively, a suction apparatus such as the Qiavac manifold or the Mobio Powervac can be used for the loading and washes. However, the column must be moved to a centrifuge for the final hard spin before elution to remove all the ethanol.

Estimation of the total RNA yield by Bioanylzer pico chip was about 1 ng. A dilution series of QRT-PCR standards puts the yield in the fmolar range.

Option 3

A simple option 3 includes precipitating the RNA in the aqueous phase using a carrier such as Glyco Blue, decanting, and resuspending the pellet directly in water. An exemplary protocol is as follows:

Add 3× volume of 4° C. 200 proof ethanol to the aqueous layer along with 15 ug of Glyco Blue (Life Technologies, AM9516) and vortex briefly to mix. Centrifuge the sample at 16,000 rcf at 4° C. for 20 minutes. Discard the supernatant and allow the pellet to air dry for 5 minutes. Resuspend the pellet in 10 uL of RNAse-Free water.

Example 2. Comparison of Alkaline and Acid Phenol Extraction Methods

The method described in Example 1 was used to extract miRNAs from plasma samples and the results were compared with miRNAs extracted with the method described in Example 1, however using phenol ph4.5 5:1 chloroform instead.

Figure 2:
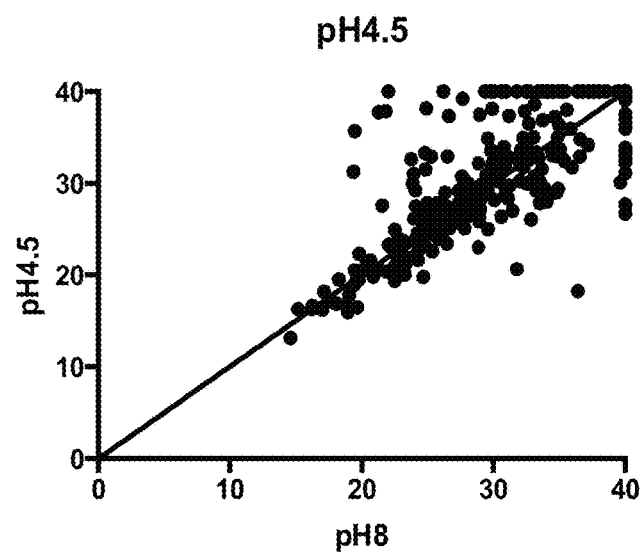
FIG. 2. A graph showing the differences between using pH8.0 phenol and pH4.5 phenol.

Ct (cycle threshold) values were determined from real time PCR using the Qiagen miScript serum/plasma 384 well array. The smaller the number, the better the signal, since the signal was detectable after amplifying for fewer cycles. Any well that did not give a detectable signal was given a "40" which is the total number of cycles run. Any cycle above 30 was not taken into account to exclude considerations of dilution partitioning in the sample, because 32 is the theoretical cycle for 1 molecule being amplified. The well volume was 10 ul. As shown in FIG. 2, most of the CTs are lower for pH 8.0.

Figure 3A:
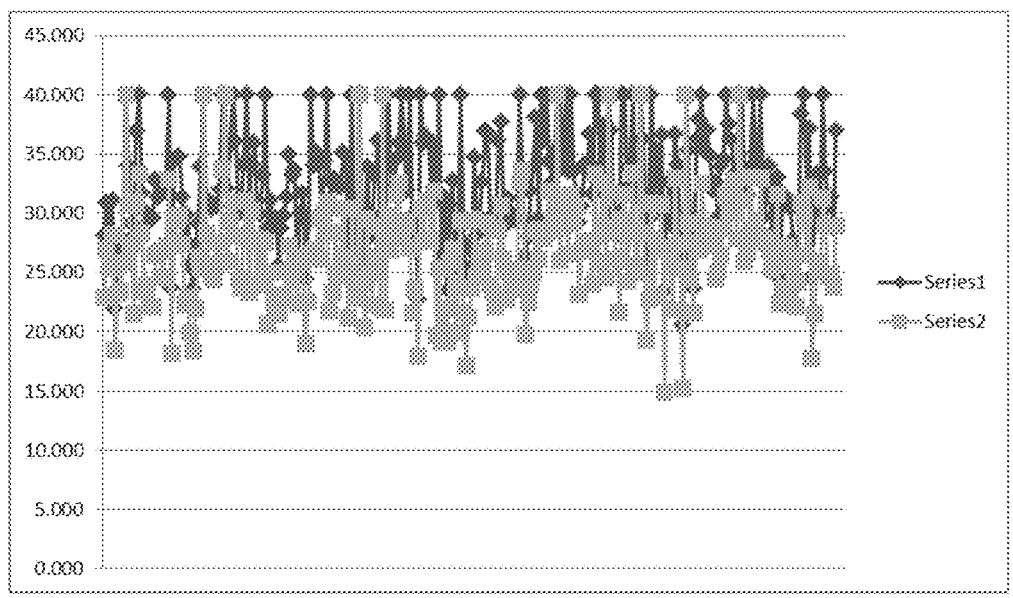
FIG. 3A. A graph showing the differences between using a standard QIAGEN miRNeasy extraction procedure (grey diamonds) and the present methods using pH8.0 phenol (black squares).
Figure 3B:
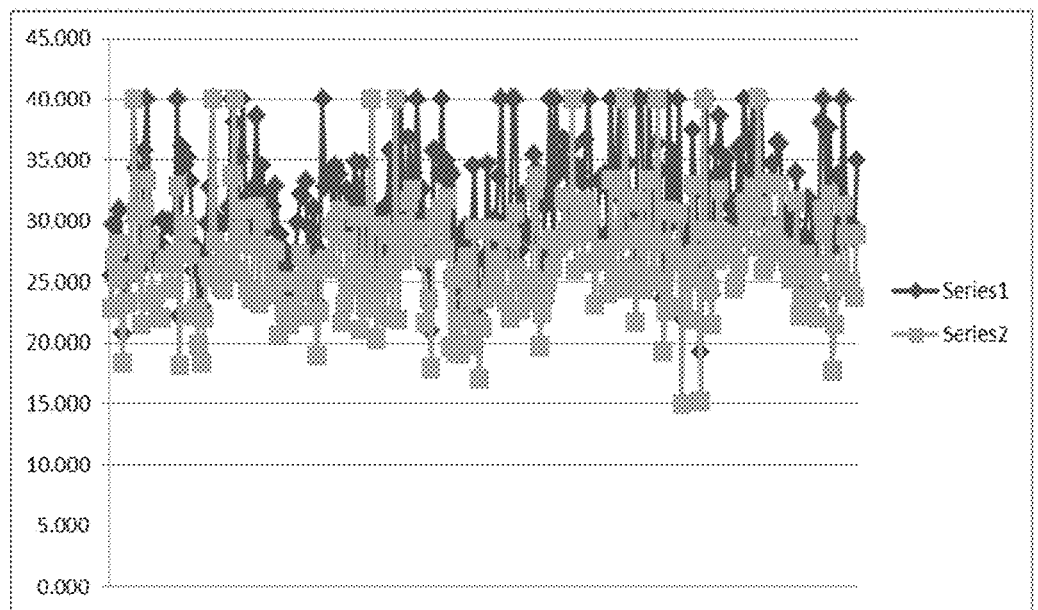
FIG. 3B. A graph showing the differences between using the present method but substituting ph 4.5 phenol (grey diamonds) and the present methods using pH8.0 phenol (black squares).
Figure 4A:
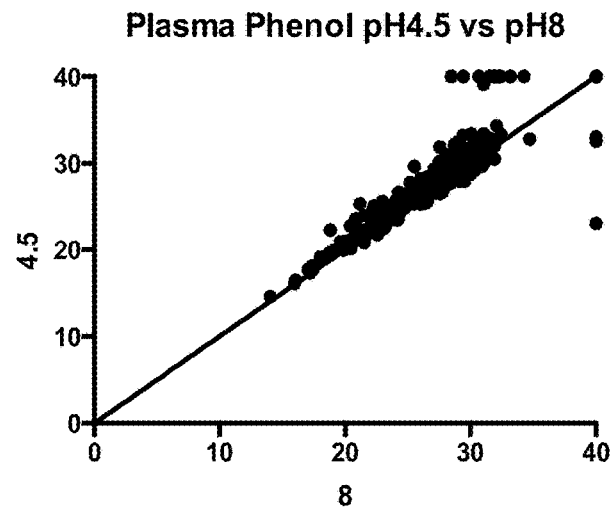
FIGS. 4A-B. Graphs showing the differences in recovery from a plasma sample using phenol at Ph4 versus ph8 (4A) and using a standard TriZOL extraction versus phenol at pH8 (4B).
Figure 4B:
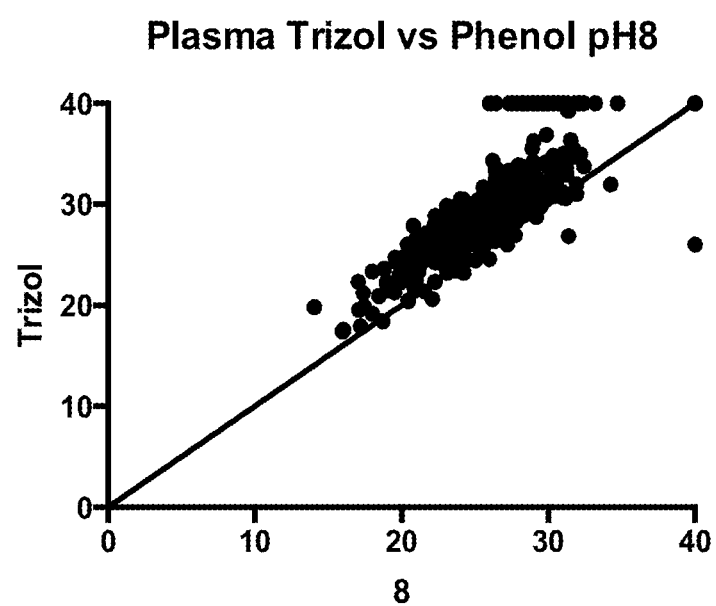
Figure 5:
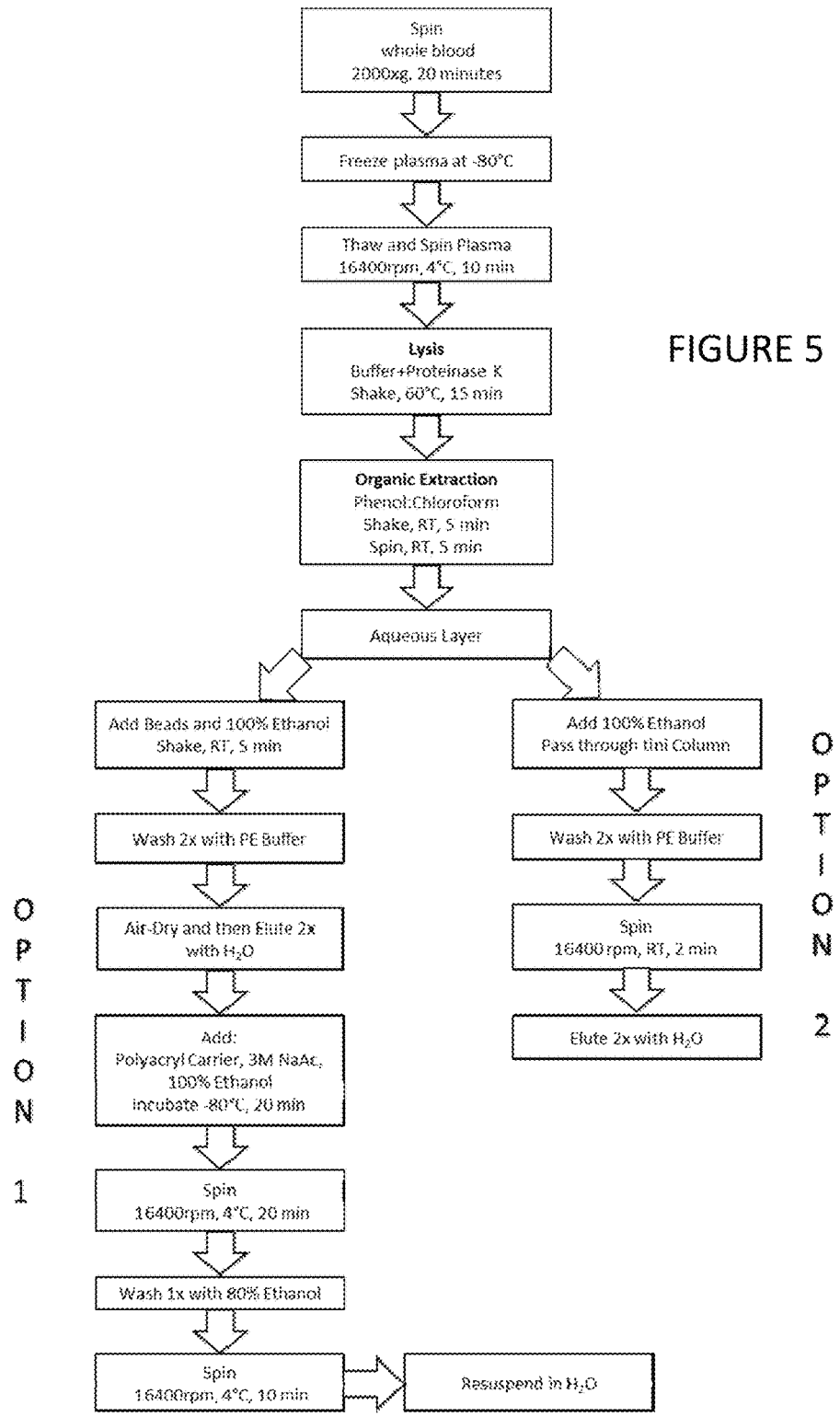
FIG. 5. A flow chart illustrating an exemplary method described herein.

Example 3. Comparison of Alkaline Phenol Extraction and a Standard Commercial Method The method described in Example 1 was used to extract small RNAs from plasma samples, and the results were compared with isolation using the QIAGEN miRNeasy Serum/Plasma kit. RT-PCR was used to compare levels as described in Example 2. As shown in FIGS. 3A (comparison with miRNeasy) and 3B (comparison with pH4.5 phenol), most of the CTs are lower.

REFERENCES

Ambros V (2001) microRNAs: tiny regulators with great potential. Cell 107:823-826.

Siow R C M, Clough G F (2012) Spotlight issue: MicroRNAs in the Microcirculation—from cellular mechanisms to clinical markers. Microcirculation 19:193-195.

Kozomara A, Griffiths-Jones S (2014) miRBase: annotating high confidence microRNAs using deep sequencing data. Nucleic Acids Res 42:D68-73.

Wang K et al. (2012) Comparing the MicroRNA spectrum between serum and plasma. PLoS ONE 7:e41561.

A mammalian microRNA expression atlas based on small RNA library sequencing. (2007) A mammalian microRNA expression atlas based on small RNA library sequencing. 129:1401-1414.

Schee K et al. (2013) Deep Sequencing the MicroRNA Transcriptome in Colorectal Cancer. PLoS ONE 8:e66165.

Valadi H et al. (2007) Exosome-mediated transfer of mRNAs and microRNAs is a novel mechanism of genetic exchange between cells. Nature Cell Biology 9:654-659.

Vickers K C, Palmisano B T, Shoucri B M, Shamburek R D, Remaley A T (2011) MicroRNAs are transported in plasma and delivered to recipient cells by high-density lipoproteins. Nature Cell Biology 13:423-433.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for isolating RNA from a sample, the method comprising:
   digesting the sample with Proteinase K in the presence of chaotropic salts and detergent;
   extracting RNA from the sample using an alkaline phenol:chloroform extraction; and
   isolating the extracted RNA from the sample.

2. The method of claim 1, wherein the phenol:chloroform is at pH 8.0.

3. The method of claim 1, wherein the sample is a sample of a biological fluid.

4. The method of claim 2, wherein the biological fluid comprises blood, plasma or serum, urine, cerebral spinal fluid (CSF) or other fluid.

5. The method of claim 1, wherein extracting RNA from the sample using alkaline phenol:chloroform extraction comprises contacting the sample with a solution comprising nuclease free water and phenol:chloroform.

6. The method of claim 4, wherein the nuclease free water and phenol:chloroform are at a ratio of at least 1:10 (vol:vol) of nuclease free water to phenol:chloroform.

7. The method of claim 4, wherein the nuclease free water and phenol:chloroform are at a ratio of at least an equal volume of nuclease free water and phenol:chloroform.

8. The method of claim 1, wherein the phenol:chloroform ratio is between 6:1 to 1:1.

9. The method of claim 1, wherein the phenol:chloroform ratio is between 5:1 to 3:1.

10. The method of claim 1, wherein the phenol:chloroform ratio is 5:1.

11. The method of claim 1, wherein lysing the sample comprises contacting the sample with a detergent buffer in the presence of Proteinase K.

12. The method of claim 10, comprising contacting the sample with at least 6 mAU of Proteinase K.

13. The method of claim 10, wherein the detergent buffer is a guanidine buffer.

14. The method of claim 5, wherein the guanidine buffer comprises Guanidine HCl 2M; Triton 1.6% (vol/vol); Tween 20 1.6% (vol/vol); EDTA 37.5 mM; and Tris pH 8.0 37.5 mM.

15. The method of claim 1, wherein isolating the extracted RNA from the sample comprises one or more of ethanol extraction; magnetic bead separation; or spin column extraction.

16. A method of detecting a level of a circulating miRNA in a subject, the method comprising:
   providing a sample comprising plasma or serum from a subject;
   lysing the sample;
   extracting RNA from the sample using ph 8.0 phenol:chloroform extraction;
   isolating the extracted RNA from the sample;
   and determining a level of the miRNA in the extracted RNA.

17. The method of claim 16, wherein determining a level of the miRNA in the extracted RNA comprises amplifying the miRNA; sequencing the RNA; hybridization; or a gene chip.

18. A method of monitoring a level of a miRNA in a subject, the method comprising:
   providing a first sample comprising plasma or serum of the human subject at a first time point;
   detecting a level of one or more circulating miRNAs in the first sample using the method of claim 1;
   providing a second sample comprising plasma or serum of the human subject at a second time point;
   detecting a level of the one or more circulating miRNAs in the second sample using the method of claim 1; and
   comparing the level of the miRNA in the first sample to the level of the miRNA in the second sample.

* * * * *

UNITED STATES PATENT AND TRADEMARK OFFICE
CERTIFICATE OF CORRECTION

PATENT NO. : 9,896,683 B2
APPLICATION NO. : 14/812694
DATED : February 20, 2018
INVENTOR(S) : Victor Ambros, Rosalind Lee and Anthony Patrick Fusco It is certified that error appears in the above-identified patent and that said Letters Patent is hereby corrected as shown below:

In the Claims

Column 10, Line 28, In Claim 16, delete "ph" and insert --pH--.

Signed and Sealed this
Nineteenth Day of June, 2018

Andrei Iancu
*Director of the United States Patent and Trademark Office*